United States Patent [19]
Atkins

[11] Patent Number: 5,280,876
[45] Date of Patent: Jan. 25, 1994

[54] LIMITED RESTRICTION QUICK DISCONNECT VALVE

[76] Inventor: Roger Atkins, 7729 South 3500 East, Salt Lake City, Utah 84121

[21] Appl. No.: 36,972

[22] Filed: Mar. 25, 1993

[51] Int. Cl.$^5$ .............................................. F16L 37/28
[52] U.S. Cl. .................................. 251/149.1; 251/144; 604/905
[58] Field of Search .................... 251/149.1, 35.7, 144, 251/342, 148, 150; 604/256, 905

[56] References Cited
U.S. PATENT DOCUMENTS

| | | | |
|---|---|---|---|
| 2,946,555 | 7/1960 | Cantor | 251/342 |
| 3,838,843 | 10/1974 | Bernhard | 251/149.1 |
| 4,106,675 | 8/1978 | Taylor | 251/342 |
| 4,167,204 | 9/1979 | Zeura | 251/149.1 |
| 4,819,684 | 4/1989 | Zaugg et al. | 251/149.1 |
| 5,061,253 | 10/1991 | Yoshida | 251/342 |
| 5,069,880 | 12/1991 | Karlson | |
| 5,087,419 | 2/1992 | Lutz | |
| 5,118,471 | 6/1992 | Anderson et al. | |
| 5,120,512 | 6/1992 | Masuda | |
| 5,203,775 | 4/1993 | Frank et al. | 251/149.1 |

Primary Examiner—A. Michael Chambers
Attorney, Agent, or Firm—M. Reid Russell

[57] ABSTRACT

A limited restriction quick disconnect valve preferably for mounting between a container, like that involved in medical instrument sterilization system, and a transfer line for passing a sterilization agent thereto. The valve is for mounting at a bulk head female connector section into the container wall and includes a stem with side ports formed therein that intersect a passage that is open to within the container, the stem for receiving, as a closure device, a resilient sleeve fitted, in sealing arrangement, thereover. A closure ring section, that is connected to the transfer line, is provided for fitting onto a retaining ring of the bulk head female connector. The closure ring section includes a cylindrical shaft that is arranged axially therein that includes a forward end for engaging and compressing the resilient sleeve when the coupling ring is fitted onto the retaining ring, the resilient sleeve when compressed to bow outward around its mid portion, lifting the sleeve interior surface off from and opening the side ports, providing a passage from the container to the transfer line. For cleaning after use, the resilient sleeve can be pulled off the stem and replaced with another resilient sleeve and the interiors of the bulk head female connector and coupling ring section are open, have no moving parts, for facilitating cleaning.

13 Claims, 3 Drawing Sheets

LIMITED RESTRICTION QUICK DISCONNECT VALVE

BACKGROUND OF THE INVENTION

1. Field of the Invention

This invention relates to valves and in particular to quick release valves that are suitable for use in medical instrument sterilization systems for releasably connecting sterilization agent inlet and exhaust lines to a removable primary sterilization chamber wherein medical instrument sterilization takes place.

2. Prior Art

Quick release valves utilized in pneumatic systems, as for example valves for connecting lines together to transfer compressed air to air driven tools, have long been known and are in common use. Such valves while well suited for providing for a compressed air or even liquid transfer have posed significant difficulties when they have been applied to medical systems, particularly medical instrument sterilization systems as the valve does not lend itself to reliable cleaning. In such systems, a sterilization agent is transferred into and from a primary sterilization chamber wherein medical instruments are sterilized and is then removable for carrying sterilized instruments to an operating room.

An example of such an medical instrument system sterilization system is shown in an earlier U.S. patent application of one of the present inventors entitled, "Ozone Sterilization System Primary Sterilization and Transport Container", U.S. patent Ser. No. 07/940,850. In which system conventional pneumatic valves are illustrated as having been utilized to provide a connection between sterilization agent lines and as quick release valves that allow for a release of the primary sterilization container for movement to an operating room. Such pneumatic valves with their arrangement of balls, seats and spring biased sleeve, however, present a number of crevices and recesses that are difficult to clean and sterilize after use. Accordingly, such pneumatic valves, though functionally satisfactory for transfer of a sterilization agent, are themselves potential sources of contamination and have not proven entirely satisfactory for inclusion with medical instrument sterilization systems.

The valve of the present invention employs a resilient sleeve as the valve closure component that is itself easily removable and replaceable. After which removal the valve body and connection components are easily broken apart and have inner cavities that are essentially smooth walled and therefor are conveniently and efficiently cleaned and sterilized, presenting a significant improvement over the pneumatic valves as have formerly been utilized. Medical instrument sterilization systems that employ sterilization agent transfer lines and valve are shown in patents to Masuda, U.S. Pat. No. 5,120,512 and to Karlson, U.S. Pat. No. 5,069,880. Also, a plurality of container and chamber arrangements for use in sterilization processes that utilize treated ozone as the effluent are shown in patents to Anderson, et al, U.S. Pat. No. 5,118,471; and to Lutz, U.S. Pat. No. 5,087,419. None of which systems, however, have utilized a quick release valve that is configured like that of the present invention.

SUMMARY OF THE INVENTION

It is a principal object of the present invention in a limited restriction quick disconnect valve to provide a valve that is suitable for use in a medical instrument sterilization system, or the like, for releasably coupling a primary sterilization chamber, wherein medical instruments are sterilized, with sterilization agent inlet and outlet lines.

Another object of the present invention is to provide a quick disconnect valve that is readily broken apart and includes a resilient sleeve as a closure member that can be removed and replaced, with the valve body components having essentially smooth interior wall surfaces that are easily cleaned and disinfected.

Another object of the present invention is to provide a quick disconnect valve for inclusion between inlet and outlet sterilization agent transfer lines and a primary sterilization chamber that is easily releasable by turning of single connection sleeve, separating the valve forward and rear components.

Another object of the present invention is to provide a quick disconnect valve that is capable of being swiftly broken down into its component parts to expose the resilient sleeve closure member that can be easily removed and replaced after the valve components have been cleaned and disinfected for remounting in the primary sterilization chamber and connection to the sterilization agent inlet and exhaust lines.

Still another object of the present invention is to a quick disconnect valve that is functionally unique over earlier pneumatic valves in that it does not involve a mechanical closure arrangement, and rather employs a replaceable resilient sleeve as the closure member that, when relaxed, as when the valve body components are separated, closes and seals off side ports that open into a passage to the primary sterilization chamber, maintaining that chamber in a sealed attitude, and when the valve body components are connected together the ends of the resilient sleeve are compressed together flexing the sleeve middle portion so as to lift the sleeve off of the side ports that are thereby opened to allow a flow through the valve.

Still another object of the present invention is to provide a make before break quick disconnect valve that has no moving parts, is a single step open or close arrangement that provides a secure sealed closure when the valve body components are broken apart and is open therethrough when the valve body components are recoupled together.

Still another object of the present invention is to provide a quick disconnect valve that is easily and inexpensively manufactured from light weight metal materials and utilizes a thick walled resilient tube section as the valve closure member that is easily and inexpensively replaced after each use.

The invention is in a limited restriction quick disconnect valve that is particularly well suited for providing a quick release coupling of a primary sterilization chamber to sterilization agent inlet and exhaust lines in a medical instrument sterilization system. Though, it should be understood, the quick disconnect valve of the invention could be employed in any number of applications where it is desired to provide a quick release valve whose components are easily connected together, is simple and inexpensive to manufacture and can be easily and reliably cleaned.

The quick disconnect valve of the invention includes a female bulk head connector arranged for mounting into a container wall, such as the wall of a primary sterilization chamber of a medical instrument sterilization system. A valve closure device, that is a section of a resilient sleeve is contained within the female bulk head connector, mounted over side ports that are formed in a stem of a forward end section of the female connector. A retaining ring, that includes a keeper turned therein, is itself turned onto the stem. Thereby, the resilient tube ends are contained between an interior wall of the female connector forward end and an opposing internal face of the keeper, the resilient tube interior surface closing over the stem side ports. A coupling ring, that includes detents that project inwardly at space points from its inner wall that ar for traveling into and along locking slots that have been formed in the retaining ring outer surface. The coupling ring in arranged with a cylindrical shaft that is open therethrough, and the section is for mounting onto the end of a transfer line. The coupling ring for coupling onto the retaining ring of the bulk head female connector, the cylindrical shaft end for traveling axially into the retaining ring, engaging and compressing the resilient sleeve end, bowing it outwardly around its mid portion to lift the resilient sleeve off of the side ports, open the valve to the liquid or gas transfer line.

As required, the quick disconnect valve of the invention can be quickly disassembled. Where valve interior cleaning and disinfecting is required, the resilient tube can be conveniently removed and replaced, opening the valve body components that have essentially smooth inner walls without crevices and therefore lend themselves to being cleaned and disinfected after use.

DESCRIPTION OF THE DRAWINGS

In the drawings that illustrate that which is presently regarded as the best mode for carrying out the invention.

DETAILED DESCRIPTION

Figure 1:
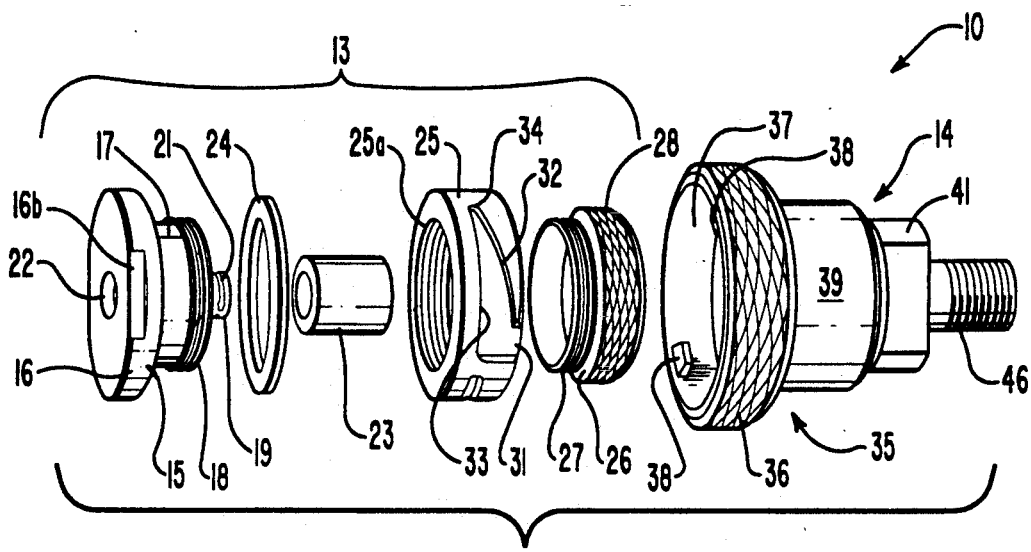
FIG. 1 shows an exploded side elevation view of a limited restriction quick disconnect valve of the invention.
Figure 2:
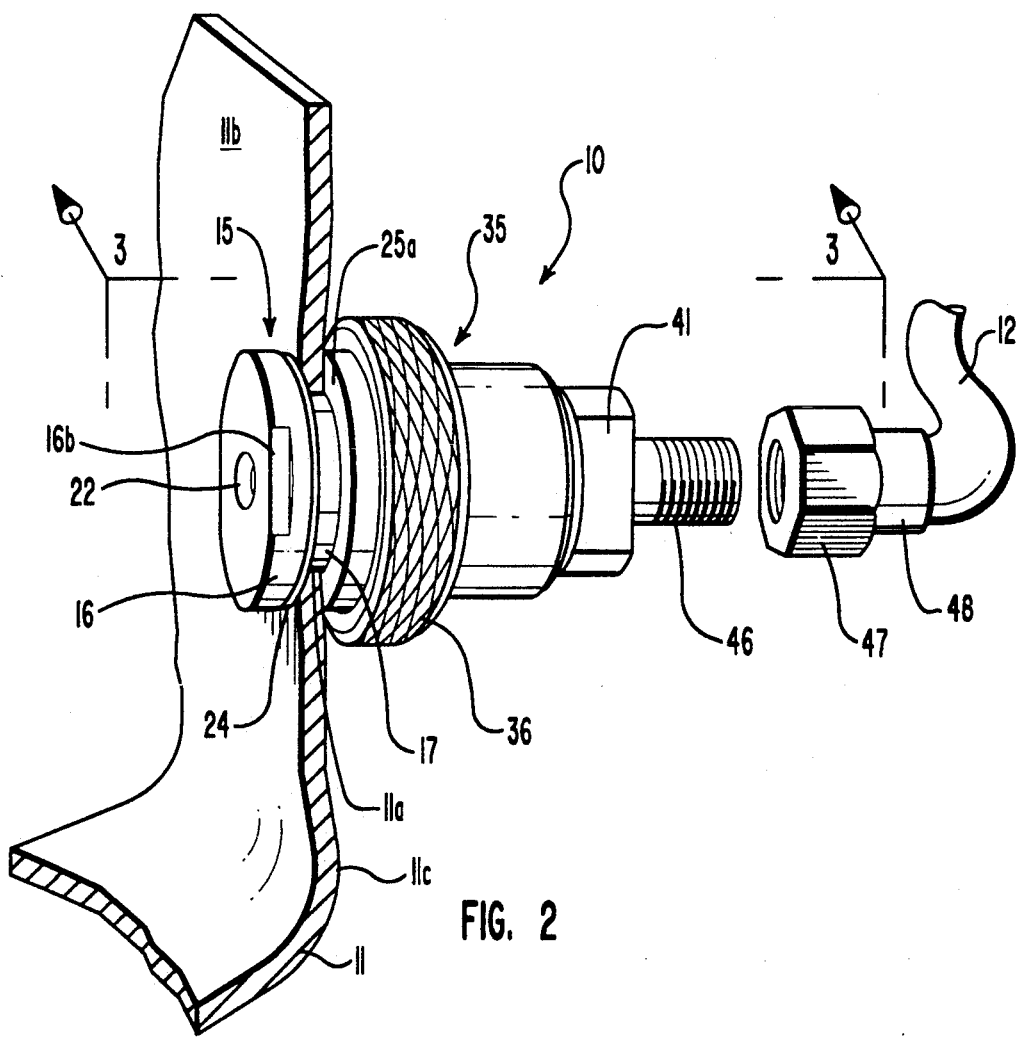
FIG. 2 shows a profile perspective view of the assembled quick disconnect valve of FIG. 1, with a bulk head female connection end shown maintained in an upright wall, that should be taken as a wall of a container, with the other valve end shown aligned for receiving a connector fitting mounted onto an end of a transfer line turned thereon.

FIG. 1 shows a profile perspective exploded view of a limited restriction quick disconnect valve 10 of the invention, hereinafter referred to as valve. The valve 10, as shown best in FIG. 2, is preferably for mounting in the side of a vessel or container, illustrated as a wall 11, for exhausting from or passing a flow of a liquid or gas into the container 11. The valve is arranged to be quickly connected and disconnected for joining the container to a transfer line 12, and provides a closure device that is removable and replaceable after each use, as needed. The valve of the invention is particularly well suited for use with a medical instrument sterilization system for releasably connecting a primary sterilization chamber to sterilization inlet and outlet lines. Though, it should be understood, the valve 10 can be used for any number of applications as a quick disconnect valve, within the scope of this disclosure.

Figure 3:
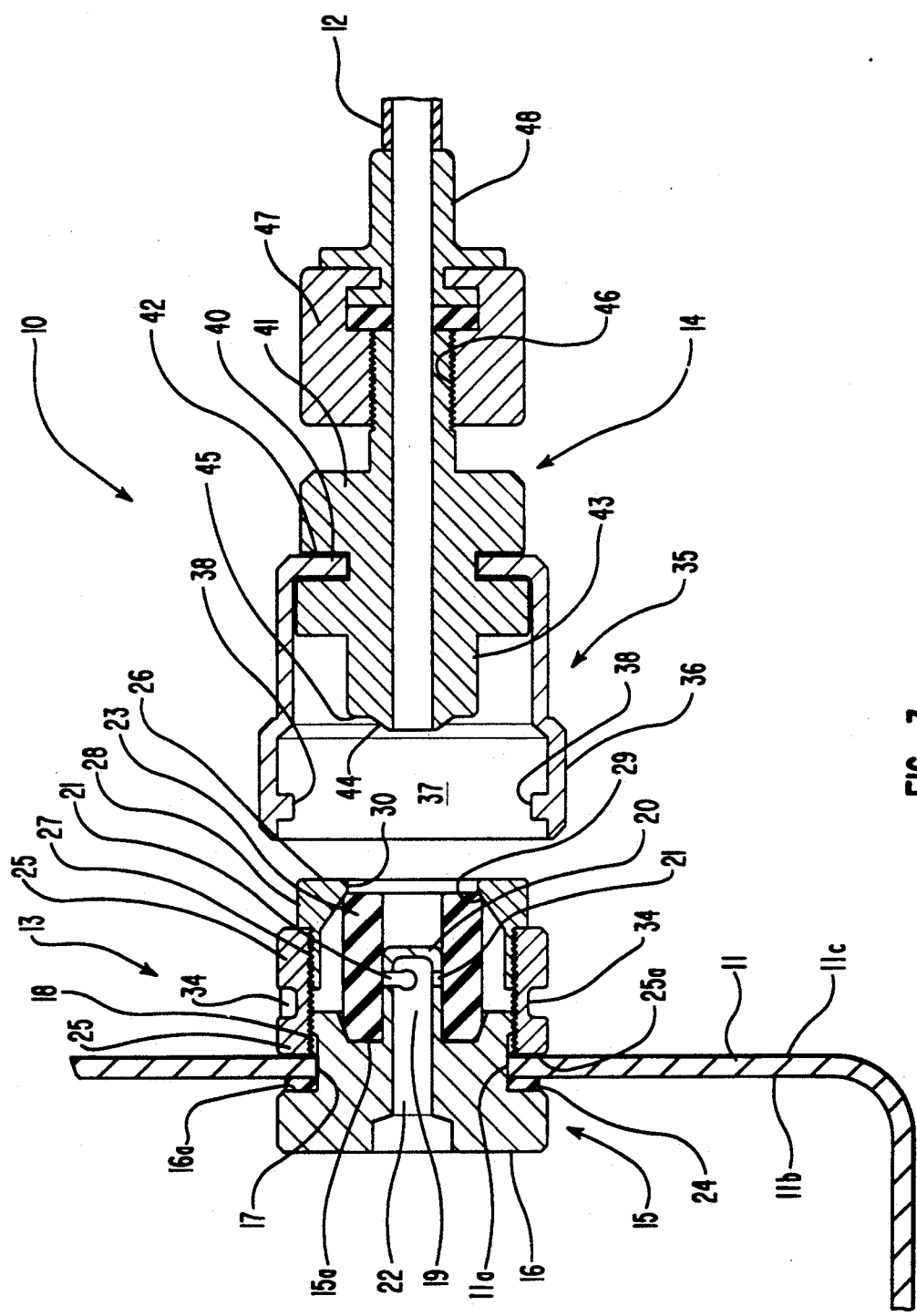
FIG. 3 shows a profile sectional view taken along the line 3—3 of FIG. 2, showing the valve body sections separated, with a coupling ring separated from a retaining ring, and showing a resilient sleeve arranged on a stem within the valve bulk head female connector, as the valve closure device, showing the resilient sleeve in a relaxed state relaxed closing off side ports in the stem of the bulk head female connection.
Figure 4:
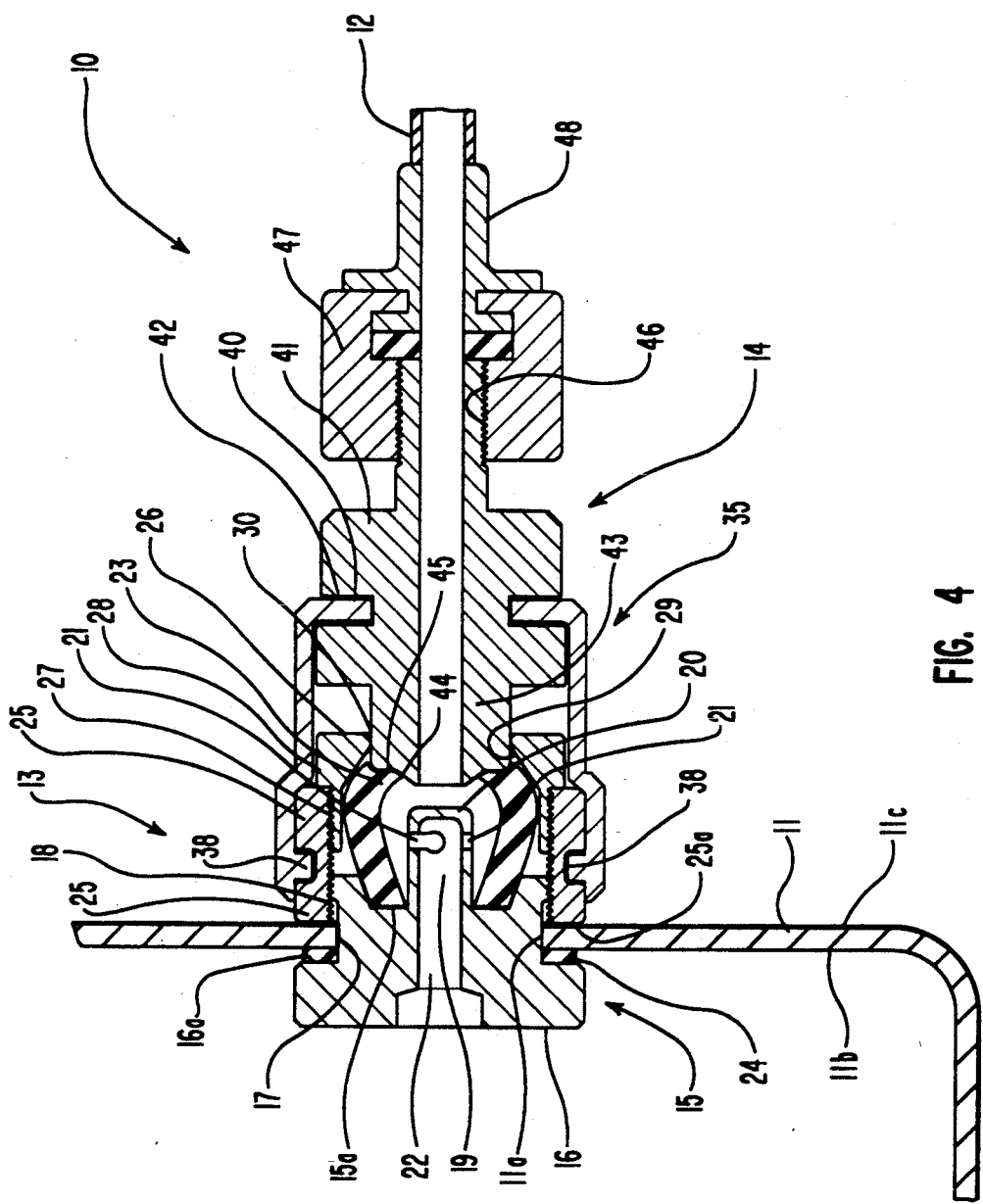
FIG. 4 shows a view like FIG. 3 except the coupling ring is shown turned onto the retaining ring, showing an end of a cylindrical shaft mounted axially in the coupling right, that is open therethrough to the transfer line, in engagement with the resilient sleeve end, compressing that resilient sleeve to bow it outwardly around its middle, and showing the resilient sleeve inner surface lifted off of the stem side ports, allowing a flow to pass from the transfer line, through the side ports into the container, illustrated as a wall section.

Shown in FIGS. 1 and 3, the valve 10 includes a bulk head female connector section 13, that receives, as illustrated in FIGS. 2 and 4, a coupling connector section 14 fitted thereto for connecting the valve 10 sections together so as to pass a flow between the container 11 and transfer line 12. The bulk head female connector section 13 includes a container mount 15 that has a flat forward face 16 and is stepped axially inwardly from the center of a rear face into a cylinder 17. The cylinder 17 is threaded at 18 around a mid section and is stepped axially inwardly, at a rear face thereof, into a stem 19. The stem 19 extends axially from the container mount 15 and is closed across its rear end 20. The stem 19 includes one or more side ports 21 that open to a center longitudinal opening 22 that opens in the center of the container mount 15 flat forward face 16.

A resilient sleeve 23 is shown best in FIG. 3, fitted over the stem 19 that is in a relaxed attitude and is shown in FIG. 4 as having been a compressed, showing the resilient sleeve bowed outwardly around its middle. The resilient sleeve 23, as shown in FIG. 3, is relaxed with the interior wall thereof in covering attitude over the stem side ports 21. Whereas, as shown in FIG. 4, with the resilient sleeve bowed outwardly around its middle, the interior wall is lifted off the side ports 21, opening them to a flow therethrough. By coupling together the bulk head female connector section 13 and coupling connector section 1 provides for bowing of the resilient sleeve 23, as shown in FIG. 4, opening the valve 10 to pass a flow therethrough, as set out in detail hereinbelow.

Shown in FIGS. 1, 3 and 4, to assembly the bulk head female connector section 13 onto container 11 a resilient sealing gasket 24 is fitted over the stem 19 and cylinder 17 to engage a rear face of the container mount 15, and the stem and cylinder are fitted into a hole 11a formed through the container 11 wall, the sealing gasket 24 to engage a container inner face 11b around the hole 11a. With the resilient sleeve 23 fitted onto the stem 19, as shown best in FIG. 3, a retaining ring 25 is fitted thereto. The retaining ring 25 is threaded internally along its length and is turned onto the cylinder 17 threads 18, until a retaining ring forward end 25a engages a container outer face 11c around hole 11. The retaining ring 25 turning on the cylinder 17 threads 18 draws the container mount thereto, compressing the sealing gasket 24 against the container inner face 11b to provide for sealing of the container mount 15 in the wall of container 11. For containing the resilient sleeve 23 a retaining ring keeper 26, that is threaded around a forward end 27 thereof, is turned into the retaining ring 25, onto the retaining ring internal threads. From the threaded forward end 27 rearwardly the keeper 26 is stepped outwardly into a finger engaging portion 28 that is preferably appropriately cross hatched for gripping by an operator for turning the keeper 26 into the retaining ring 25 internal threads. The keeper 26 is centrally open axially, and that passage wall is sloped at 29, from a greater diameter at approximately its middle area, to a lesser diameter opening 30 at the keeper rear face. The keeper opening 30 is of a lesser diameter to that of the resilient sleeve 23 and is for retaining an end of that resilient sleeve 23 in a cavity that is formed within the retaining ring 25, between the keeper 26 sloping inner wall 29 and a cavity 15a in the container mount 15 rear face that is formed the stem 18. The stem 18, as shown, to include the center passage 22 therethrough that is closed off at end 20. Shown best in FIG. 3, the resilient sleeve 23 is maintained in a relaxed state, the inner wall thereof sealing over the side ports 21 of stem 19, closing off passage 22 that opens into the container 11.

Coupling connector section 14 that is coupled the transfer line it provided for coupling to the bulk head female connector section 13. The coupling connector, as shown in the drawings, includes a coupling ring 35 on a forward end thereof. The coupling ring 35, in turn, includes a joining ring 36 that has a smooth inner wall 37 and is of a diameter to fit over the retaining ring 25. Detents 38 are formed in the coupling ring 35 inner wall 37 to extend inwardly, at spaced intervals, from around that inner wall. The coupling ring 35 is for sliding over and locking to the retaining ring 25, with the coupling ring detents 38 to align with and travel into a groove opening 31, that is formed as a groove in the retaining ring 25 outer surface, in the shape of a right triangle. For connecting the rings together, the coupling ring is urged over the retaining ring, the coupling ring detents sliding into the grooves 31. The coupling ring 35 is then turned such that each detent 38 will slide along a groove sloping side 32, traveling between that sloping side 32 and a straight groove side 33, that is the triangle base, to a groove end 34 that is the junction of the groove sloping and straight sides. The valve 10 bulk head female connector section 13 and the coupling connector section 14 are thereby joined together as shown in FIGS. 2 and 4.

As shown best in FIGS. 3 and 4, the coupling ring 35, is essentially a thin walled cylindrical shell that is open therethrough. The coupling ring 35 includes the roughened surface 36 and is stepped inwardly, at approximately a mid point into a cylindrical body section 39. The cylindrical body section 39, in turn, is turned inwardly into a right angle foot 40 as its rear end, which right angle foot 40 is open through the center thereof. The right angle foot is for fitting in sealing, arrangement into a groove 42 that has been formed around a mid-section of a plug 41 that formes the rear portion of the coupling ring section 14. A forward end of plug 41 is shown, in FIGS. 3 and 4, as a cylindrical shaft 43 that is of a diameter to travel through the opening 30 in the keeper 26 rear end, traveling between the ends of the sloping surface 29 that contain the end of the rear end of the resilient sleeve 23. The cylindrical shaft 43 forward end face is formed to have a concave to flat section 45 formed around the outer one quarter to one third of the shaft end face to the shaft circumference and slopes therefrom toward the longitudinal axis outwardly into a frustum of a cone section 44 that intersects a longitudinal hole through the plug 41. Shown best in FIG. 4, as the coupling ring 35 is turned onto the retaining ring 25 the cylinder shaft 43 frustum of a cone section 44 travels into the resilient sleeve 23 center opening. The resilient sleeve end area is captured by the shaft face flat section 45, prohibiting passage of the cylindrical shaft into the resilient sleeve as the resilient sleeve is uniformly compressed against its opposite end that is seated against the container mount 15 cavity 15a. With continued movement of the shaft 41 against the resilient sleeve 23 end, the resilient sleeve is further compressed, bowing the middle sleeve area outwardly, as shown in FIG. 4, and lifting the sleeve inner surface off of the side ports 21. Uncovering of the side ports 21 opens the stem 19 longitudinal passage 22 to the longitudinal passage through the plug 41.

Shown best in FIGS. 3 and 4, the plug 41 rear end 46 is threaded for receiving a coupling nut 47 turned thereon the coupling nut 47, in turn, is fitted onto to a spindle 48 that connects to the transfer line 12, the nut 47 to turn freely on the spindle 48 and includes a sealing washer or gasket between which the opposing spindle face and a rear face of the plug 41. The nut 47 and spindle 48 mounting, as shown, is essentially a standard pressure line coupling. With the nut 47 arranged to turn freely on the spindle, the coupling ring 35 is allowed to turn onto the retaining ring 25, as described above.

For mounting the bulk head female connector 13 in the container wall 11 the container mount 15 flat forward face section 16 includes a pair of straight notches 16a that are formed in opposite sides of the section and are for receiving a wrench type spanning tool, not show, fitted thereacross. To install the valve bulk head female connection 13, the stem 19, with the resilient sleeve 23 fitted thereto, that extends axially from the cylinder 17 whereon is positioned the sealing gasket 24, is fitted through the container wall hole 11a. A spanning tool, not shown, is fitted onto notches 16a, so as to hold the container mount 15 in place, and the retaining ring 25 is turned over the cylinder 17 threads 18. The retaining ring 25 is turned onto cylinder threads 18 to where the retaining ring forward face 25a engages the container wall surface 11c around the container hole 11a. The container mount rear face 16a is thereby drawn against the sealing gasket 24, compressing the gasket to where it seals the container mount 15 in the container hole 11a. Assembly of the bulk head female connector 13 in the container wall 11 is completed by turning of the keeper 26 onto the retaining ring 25 inner threads, the keeper sloping rear wall 29 engaging and fitting snugly against the resilient sleeve 23 end, as shown in FIG. 3.

With the bulk head female connector 13 mounted to the container 11, as describe above, the coupling ring 35 can then be fitted onto the retaining ring 25 and turned. In which fitting and turning, the retaining ring detents 38 travel into the groove 31 opening, along the groove sloping side 32 to the groove end 34. A connection of the coupling ring 35 onto the retaining ring 25 is thereby provided, in which connection, as shown in FIG. 4, the cylindrical shaft 43 end face engages the resilient sleeve 23 end and compresses it to where it bows outwardly around its mid-opposite section. The resilient sleeve inner surface is thereby lifted off of the stem side ports 21, opening the valve to passage between the container 11 and transfer line 12.

Where, for example, the container 11 is a primary sterilization chamber of a medical instrument sterilization system, after performance of a sterilization cycle, the connecting ring 35 can be turned off of the retaining ring 25, releasing the compressive force off from the resilient sleeve 23 end. The resilient sleeve is thereby relaxed to the attitude shown in FIG. 3, the resilient sleeve inner surface engaging to seal over the side ports 21. The primary sterilization chamber can then be moved, in a sealed state, to an operating room, or the like, where it is opened and the sterilized medical tools removed for use.

After use, as described above, and prior to use in another sterilization cycle, the primary sterilization chamber that the valve bulk head female connector 13 is mounted to may be cleaned and disinfected, which cleaning and disinfecting may include cleaning the bulk head female connector 13. In such cleaning and disinfecting, as required, the resilient sleeve 23 may be removed and replaced. Which removal and replacement involves turning the keeper 28 out of the retaining ring 25 to afford access to the resilient sleeve 23 that can then be pulled off from the stem 19 and replaced with a new resilient sleeve 23. With the resilient sleeve 23 removed the bulk head female connector is open and has essentially smooth interior surface that can be conveniently swabbed out with a disinfectant, or the like. Similarly, the coupling ring 35 is when removed from the retaining ring 25 is essentially open, contains the cylindrical shaft 43 only, and can therefore also be conveniently swabbed out with a disinfectant. Should a more complete sterilization of the bulk head female connector 13 be required, the retaining ring 25 can be turned off of the threads 18 of cylinder 17, releasing the container mount 15, the bulk head female connector 13 thereby broken into individual components that are easily sterilized and then reassembled.

The valve 10 of the invention has been described as being for use as a quick disconnect valve for connecting a primary sterilization chamber into a transfer line for transferring a sterilization agent. It should, however, be understood that the valve 10 is suitable for use as a replacement for most quick disconnect valves as are currently available. It should therefore be understood that the described use for valve 10 set out herein is made for example only.

In practice, the components of the limited restriction quick disconnect valve of the invention have been fabricated from a light weight aluminum metal, and a resilient tube manufactured from a silicone plastic material has been utilized as the resilient tube 23, Through, it should be understood, other appropriate materials could be used to construct components of the valve 10 of the invention, within the scope of this disclosure.

While a preferred form and embodiment of our invention in a limited restriction quick disconnect valve and its use have been shown and described herein, it should, however, be understood that the present disclosure is made by way of example only and that variations to the described invention are possible within the scope of this disclosure without departing from the subject matter coming within the scope of the following claims and a reasonable equivalency thereof, which claims I regard as my invention.

I claim:

1. A limited restriction quick disconnect valve comprising, a bulk head connector section that includes a mounting device, with means for securing it to a flow receiving arrangement as a valve forward end, that has a cylindrical segment extending axially from a rear surface thereof that includes a means for mounting a retaining ring thereon and is stepped inwardly into a stem that extends axially from a rear face of said cylinder segment, with a center longitudinal opening formed from said mounting device into said stem, and at least one side port formed into said stem to said center longitudinal opening; a retaining ring that includes, on its interior surface, a means for coupling said retaining ring onto said cylindrical segment, and includes a means for receiving and coupling to a coupling ring section fitted thereover; a keeper means, for mounting in said retaining ring, that is centrally open and includes means for retaining a resilient sleeve as a valve closure device on said stem within said retaining ring; a resilient sleeve; and a coupling ring section that is a cylinder with a coupling ring formed on a forward end, said coupling ring including means for fitting into and coupling to said retaining ring means, for coupling them together, and is stepped inwardly into a cylindrical center section that terminates in a means for pivot connection to a cylindrical plug; a cylindrical plug that is open longitudinally therethrough and includes pivot coupling means formed around a plug center portion that is for receiving, as a sealed pivot coupling, said coupling ring means for pivot connection to said plug pivot coupling means, said plug including a cylindrical shaft extending axially from said plug forward end that has a diameter to fit through said keeper central opening and has a forward face for engaging and compressing said resilient sleeve end when said coupling ring is joined to said retaining ring, and said plug rear end includes a means for receiving a transfer line mounted thereto.

2. A limited restriction quick disconnect valve as recited in claim 1, wherein the bulk head female connector mounting device is a container mount that is a disk with a flat forward face wherefrom the cylindrical section extends axially from said disk rear face.

3. A limited restriction quick disconnect valve as recited in claim 2, wherein the longitudinal opening extends from the center of said disk into the stem; and said disk forward face includes a pair of straight parallel grooves formed in opposite edges thereof.

4. A limited restriction quick disconnect valve as recited in claim 1, wherein the cylindrical segment is externally threaded from approximately a mid-section to a rear end adjacent to the stem as the means for mounting the retaining ring; and the retaining ring is threaded internally along its length as the means for coupling to turn onto said cylindrical segment.

5. A limited restriction quick disconnect valve as recited in claim 4, wherein the keeper means is a cylindrical section that is open axially and is threaded externally along a forward end for turning into the retaining ring internal threads; and the means for retaining the resilient sleeve end is rear end interior wall that slopes from the axial opening toward said forward end to approximately a mid point of said cylindrical section.

6. A limited restriction quick disconnect valve as recited in claim 1, wherein the resilient sleeve is longer than the stem whereon it is fitted such that a compression of said resilient sleeve end will bow said resilient sleeve around a mid portion thereof, lifting said resilient sleeve interior surface off of the side port.

7. A limited restriction quick disconnect valve as recited in claim 1, wherein the means for receiving and coupling to the coupling ring are a pair of equally space apart grooves, each formed in retaining ring outer surface in the shape of a right angle triangle that is open to the coupling ring rear edge that is the junction of the groove opposite and hypotenuse triangle sides.

8. A limited restriction quick disconnect valve as recited in claim 7, wherein the coupling ring means for coupling to said retaining ring are a pair of equally spaced apart detents that each project inwardly, at right angles, the interior surface of the coupling ring that are for fitting into the retaining ring groove opening and travel along the hypotenuse side to the junction of the hypotenuse side and the adjacent sides of said groove as said coupling ring in turned onto said retaining ring, coupling said rings together.

9. A limited restriction quick disconnect valve as recited in claim 8, wherein the coupling ring is scored around its outer surface for facilitating gripping and turning by an operator.

10. A limited restriction quick disconnect valve as recited in claim 1, wherein the means for pivot connection of the coupling ring section to the cylindrical plug is an inturned rear end of said coupling ring section that is open centrally and is for fitting into a groove that is formed around the circumference, at a middle portion, of the cylindrical plug as the pivot coupling means.

11. A limited restriction quick disconnect valve as recited in claim 1, further including, formed on the plug flat forward face, a raised portion projecting outwardly from around the longitudinal opening through the plug.

12. A limited restriction quick disconnect valve as recited in claim 1, wherein the means for receiving a transfer line mounted to the plug rear end are external threads formed along said plug rear end.

13. A limited restriction quick disconnect valve as recited in claim 12, further including, flat parallel sections formed in the plug rear portion, adjacent to the plug rear end external threads, for receiving a wrench type tool fitted thereover.

* * * * *